(12) United States Patent
Nydén et al.

(10) Patent No.: US 7,531,581 B2
(45) Date of Patent: May 12, 2009

(54) METHOD AND USE OF ACIDIFIED MODIFIED POLYMERS TO BIND BIOCIDES IN PAINTS

(75) Inventors: Magnus Nydén, Billdal (SE); Camilla Fant, Kullavik (SE); Krister Holmberg, Gotenburg (SE); Lars Swanson, Ojesjo (SE)

(73) Assignee: I-Tech AB, Göteborg (SE)

( * ) Notice: Subject to any disclaimer, the term of this patent is extended or adjusted under 35 U.S.C. 154(b) by 344 days.

(21) Appl. No.: 11/372,522

(22) Filed: Mar. 10, 2006

(65) Prior Publication Data
US 2006/0223906 A1    Oct. 5, 2006

Related U.S. Application Data

(60) Provisional application No. 60/661,290, filed on Mar. 11, 2005.

(51) Int. Cl.
C09D 5/16    (2006.01)

(52) U.S. Cl. .................... 523/123; 523/177
(58) Field of Classification Search ........... 523/122, 523/127
See application file for complete search history.

(56) References Cited

U.S. PATENT DOCUMENTS 6,271,283 B1 *   8/2001   Shimada et al. ............. 523/122
6,762,227 B1 *   7/2004   Elwing et al. ............... 524/106

* cited by examiner

Primary Examiner—Kriellion A Sanders
(74) Attorney, Agent, or Firm—Lynn E. Barber

(57) ABSTRACT

The invention herein relates to the method and use in an antifouling paint that specifically and efficiently impede settlement of for example barnacles on aquatic structures, using imidazole containing compound, such as Medetomidine, bound to a sulfonated, acid sulphate ester, phosphonic acid, carboxylic acid or acid phosphate ester modified polymer backbone such as polystyrene or acrylate polymers. The aim is to employ the biocide-polymer complexes as additives in a self-polishing paint for controlled release purposes.

14 Claims, 2 Drawing Sheets

METHOD AND USE OF ACIDIFIED MODIFIED POLYMERS TO BIND BIOCIDES IN PAINTS

CROSS-REFERENCE TO RELATED APPLICATIONS

This is application claims priority from U.S. provisional application Ser. No. 60/661,290 filed Mar. 11, 2005, which is incorporated herein by reference.

BACKGROUND OF THE INVENTION

1. Field of the Invention

Polystyrene-block-poly(ethylene-ran-butylene)-block-polystyrene (der-PS) has the possibility to generate an ionic bond between, for example, the sulfonic acid groups and basic nitrogens in medetomidine. This is a feature of particular interest in attempts to develop an efficient antifouling surface and improve the performance of antifouling paints with regard to distribution and fixation of the biocide in a paint matrix for even release and effect in hindering for example barnacle colonization. Equivalent systems can be used with the same polymer interaction for even release of a biocide in other paints than marine antifouling paints.

2. Description of the Related Art

The growth of biofouling organisms on underwater structures is a costly and hazardous problem in both marine and freshwater applications. The presence of fouling organisms such as barnacles, algae, tube worms and the like causes economic damage in various ways: for example attachment to the hulls of ships reduces fuel efficiency and causes loss of profitable time because of the need to clean the hulls. Similarly, the attachment of these organisms to cooling water equipment decreases heat conductivity, which eventually reduces the cooling power of the equipment and drives up costs. Also other marine industries and installations, e.g. aqua culture equipment and oil/gas off-shore installations and plants have significant problems with marine biofouling.

Mechanical cleaning of marine surfaces has been introduced as an alternative to toxides and biocides. Notably, water jet cleaning and mechanical cleaning using brushes are in use. The majority of these methods are, however, work-intensive and therefore expensive.

The most efficient antifouling paints have been "self-polishing copolymer" paints based on a polymeric binder to which biocidal organotin, in particular tributylin are chemically bound and from which biocidal organotin is gradually hydrolyzed by seawater as described for example in UK patent GB-A-1457590. These organotin copolymer paints prevent fouling by releasing the organotin compounds during hydrolysis of the polymer. The outermost paint layer becomes depleted of biocides and is swept of the surface of the hull by the movement of the ship through water. Organotin copolymer paints also contain copper oxide pigment which is effective against biofouling against marine organisms while the tributylin acts as a protection from slime and weed.

Paint containing organotin compounds, in particular tributylin have proven to cause negative environmental consequences, harming sea life, causing deformations in oysters and sex changes in whelks. It have been noted that organotin compounds are degraded slowly, and as a consequence these compounds have been accumulated in the sediments in localized areas. Several countries and international organizations have therefore introduced restrictions and prohibitions over their use and further restrictions are expected. Sale and application of tributylin antifouling is to cease, under the International Maritime Organization (IMO) Antifouling System Convention agreed in October 2001. The treaty calls for the ban on application from 1 Jan. 2003 and total prohibition on hulls by 1 Jan. 2008.

With the recent restrictions on the use of these toxic coatings in many countries, the boat and ship owners have fallen back to the technically inferior but less toxic copper oxide based coatings. The life of copper oxide based coatings rarely exceeds 2 years in normal fouling conditions compared to 5 years with self-polishing tributylin. Dissatisfaction existed because copper oxide based coatings did not satisfy the boat and ship operators and owners. Neither did it satisfy environmental protection organizations because of its toxicity to the environment. When the copper compounds are used in reduced concentrations for ecological reasons these paints need however booster biocides against barnacles and algae to achieve performance acceptable for ship owners and other types of marine industries.

Recent progress within the field of self-polishing paints includes the use of a zinc acrylate copolymer utilizing ion exchange as the release mechanism.

Concern for the possible effects of antifoulant toxicants on the environment has encouraged the development and use of systems which attempt to control fouling through surface modifications; for example, prevention of attachment through the use of silicone or fluorine containing polymers having non-stick or release properties, described for example in the following patent documents WO-0014166A1, US92105410, JP53113014, US92847401, DE2752773, EP874032A2, and EP 885938A2. It has been shown that these paints tend to be fragile, resulting in cracking and peeling of the surface.

A new alternative technology was introduced early in the 1990s. Although this was also said to be self-polishing technology, the process to obtain this was no longer through hydrolysis of a polymer. Instead combinations of different water sensitive and partly water soluble binders such as rosin, alone or mixed with acrylates as described in e.g. European patent EP0289481, EP526441 were used. The experience has shown that these paints have not been able to provide the same high and reliable performance as the hydrolyzing organotin-based paints.

Lately new polymers have been developed, based on the same principles as the organotin polymers, i.e. hydrolysis of an insoluble polymer to provide a slightly water soluble product. Among these are e.g. the self-polishing polymers described in WO8402915. Instead of incorporating organotin groups in the polymer chain, this describes the incorporation of organosilyl groups. Experience has shown that these paints have many of the properties associated with the organotin copolymer technology. However, it has also been found that over a long period cracking and peeling on the surface these paints may occur. This is caused by the leaching of soluble components, resulting in the formation of a residual layer that has a different composition than the original paint.

An approach to solve this has been to modify the silyl polymer with different co-monomers, described in EP0646630, EP1016681 and EP1127902. Another approach has been to include fibres to strengthen and increase the cohesive strength in the whole paint and particularly all the residual layer formed as described in WO0077102. A third approach has been to develop a paint wherein mixtures of organosilyl copolymers and rosin have been used to reduce the build up of this residual layer. This has been described in EP0802243. The use of low molecular plasticizers, more specifically chloroparaffines, has also been employed. This is described in EP0775733. Also sulfonic acids have previously been used in antifouling paints, such as in U.S. Pat. No.

6,627,675, but then to improve the self polishing characteristics of the paint, but not coupled to a biocide for even release as in the present invention.

Along the Swedish west coast as well as along the coasts of the North Atlantic Ocean, barnacles and algae are an economic and technical problem. The fully grown barnacle is a stationary crustacean, characterized by a centimeter sized cone shape and enclosing layers of calcinous plates. The mechanical strength of the animal's attachment to solid surfaces is very high, which is why it is difficult to mechanically remove barnacles from solid surface. The animal undergoes different development stages as free-swimming larvae, where the last larva stage is referred to as the cyprid stage. The cyprid screens solid surfaces suitable for settling with the help of a nervous protuberance. In connection with settling, the "settling-glue" referred to as balanus cement is secreted from specialized glands localised to the protuberance and the animal thereby settles to the solid surface. After settlement the animal undergoes a metamorphosis into an adult and stationary animal. When using an old copper leaking paint, with high concentration of copper, one of the first organisms to foul is barnacles.

Algae are also relatively insensitive to copper and the amount of leaking copper needed to inhibit fouling of algae is high. Therefore, copper-containing marine antifouling paints are "boosted" by some manufacturers with more specific algicides. The algicides inhibit the zoospores to attach or inhibit the photosynthesis. Both methods give the result of reduced algae fouling.

A future antifouling paint, boosted with a biocide, should act with high specificity i.e. only target fouling organisms being affected, leaving other marine mechanisms unharmed. The paint should also be designed to attain a controlled release of the active substance. An efficient approach to accomplish a controlled release is by the formation of a bond to a large molecule. Due to a large size and low mobility of a large molecule the biocide diffusion through the paint film can be restricted and thereby have a release rate which is only dependent on the polishing rate of the self-polishing paint. Furthermore the biodegradation of the antifouling agent is another important aspect in order to prevent accumulation in water and sediments and thus affecting the marine environment rather than the target biofouling organism alone.

Several compounds have been presented with antifouling activity. Among those compounds are pharmacological agents with known pharmacological profiles in vertebrates. It has been reported that a selection of pharmacological compounds, that act upon serotonin and dopamine neurotransmitters has the ability to either impede or promote the attachment of barnacles. Serotonin antagonists, such as Cyproheptadine and Ketanserin, and dopamine agonists, such as R (−)-NPA and (+)-Bromocriptine, have exhibited inhibitory properties. Another pharmacological agent that has proven to be an efficient inhibitor with regards to barnacle settlement is the highly selective alpha2-adrenoreceptor agonist Medetomidine or (S,R)-4(5)-[1-(2,3-dimethylphenyl)ethyl]-1H-imidazole. The larval settlement is impeded already at low concentrations, 1 nM to 10 Nm. Medetomidine belongs to a new class of alpha2-receptor agonists containing a 4-substituted imidazole ring with, high selectivity towards 2-adrenoreceptors. Receptors affected by catecholamine neurotransmitters, such as norepinephrine and epinephrine, are termed adrenergic receptors (or adrenoceptors) and can be divided into alpha- and beta-subclasses. The alpha2-adrenoreceptors are involved in the autoinhibitory mechanism of neurotransmitter release and play a significant part in the regulation of hypertension (high blood pressure), bradycardia (reduced heartbeat rate) and even regulation of alertness and analgesia (reduced sensitivity to pain). Medetomidine has been studied in human clinical trials and has also been used as anaesthetics for animals with the (S)-enantiomer, Dexmedetomidine, being the active component.

It is therefore an object of the invention to provide a method of binding biocides in paints using Medetomidine bound to a modified polymer backbone to better control release of the biocide. Other objects and advantages will be more fully apparent from the following disclosure and appended claims.

SUMMARY OF THE INVENTION

The invention herein relates to the method and use in an antifouling paint that specifically and efficiently impede settlement of, for example, barnacles on aquatic structures, using imidazole containing compound, such as Medetomidine, bound to a sulfonated, acid sulphate ester, phosphonic acid, carboxylic acid or acid phosphate ester modified polymer backbone such as polystyrene or acrylate polymers. The aim is to employ the biocide-polymer complexes as additives in a self-polishing paint for controlled release purposes.

DETAILED DESCRIPTION OF THE INVENTION AND PREFERRED EMBODIMENTS THEREOF

Figure 1:
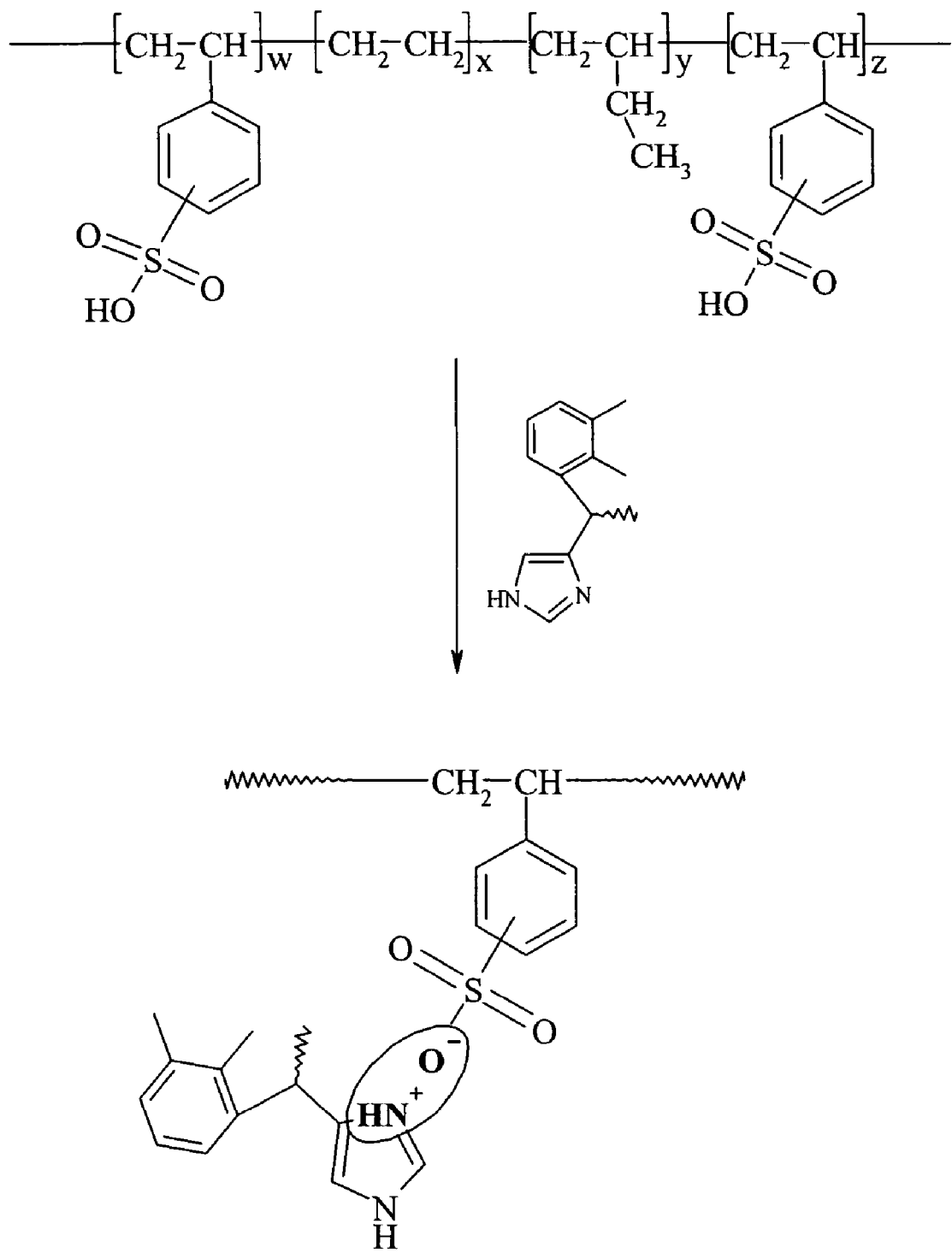
FIG. 1 shows the formation of Medetomidine-sulfonated der-PS ion pair (shown in the circle) via a proton transfer from the sulfonic acid group to the imidazole moiety.

Polystyrene-block-poly(ethylene-ran-butylene)-block-polystyrene (der-PS) has the possibility to generate an ionic bond between, for example, the sulfonic acid groups and basic nitrogens in medetomidine. This is a feature of particular interest in attempts to develop an efficient antifouling surface and improve the performance of antifouling paints with regard to distributed fixation of the biocide in the paint matrix for even release and effect in hindering, for example, barnacle colonization. Equivalent biocide systems can be used with the same polymer interaction for even release in other paints than marine antifouling paint.

Polystyrene-block-poly(ethylene-ran-butylene)-block-polystyrene complex provides a great number of binding sites for medetomidine and a high amount of medetomidine can be bound. As a result the concentration of medetomidine will be equal in the entire paint film. Thereby the distribution will be at a uniform level and a minimum amount of medetomidine will be needed to achieve even antifouling effects over the lifespan of the applied paint.

One object of this invention is to create an antifouling method requiring decreased biocide dose which is ecologically and economically advantageous. In order to improve the performance and to reduce the effect on the environment, it is important to have a proper control of the release of the antifouling substance from the paint film. The medetomidine molecule bound to Polystyrene-block-poly(ethylene-ran-butylene)-block-polystyrene is a compound that leaks out of the paint into water in a controlled fashion. The medetomidine molecule bound to Polystyrene-block-poly(ethylene-ran-butylene)-block-polystyrene has excellent dispersion stability because of its large size, compared to the medetomidine particle alone. By size property the Polystyrene-block-poly(ethylene-ran-butylene)-block-polystyrene-medetomidine particles are stationary in a SPC paint film and do not leak out into the water. This system will attain a release rate only dependant on the polishing rate of the SPC paint. As a consequence the concentration of antifouling particles in the paint film remains homologous during the "lifetime" of the paint.

Recent studies within the field of fuel membranes have reported that polymer membranes containing, for example, sulfonic acid groups can generate ionic crosslinking with polymers containing heterocyclic rings, such as imidazole and pyridine. The crosslinking reduces the effect of water uptake during proton conductivity reactions (Kerres, J.; Ullrich, A.; Meier, F.; Häring, T. Synthesis and characterization of novel acid-base polymer blends for application in membrane fuel cells. Solid State Ionics 1999, 125, 243-249). The formation of the ionic pair occurs via a proton transfer from the sulfonic acid group to the more basic nitrogen of the heterocyclic ring (for the cases of heterocyclic rings containing several nitrogens). The more basic nitrogen is also involved in coordination to transition metals. These reports indicate that Medetomidine has the possibility to form an ionic bond with sulfonated der-PS (FIG. 1). Upon exposure to water two separate ionic species will be formed by hydration. However, in an organic non-polar solvent (such as o-xylene, a common solvent in paint formulations) the dissolution process is not likely to take place. This opens the possibility of sustaining a controlled release paint system by employing the Medetomidine-sulfonated der-PS interaction. The Medetomidine-polymer ion pair will only be dissolved at the actual film surface, when in contact with water, resulting in the release of Medetomidine.

The sulfonated polymer binds to Medetomidine with a strong interaction and almost irreversibly in xylene. In water the, the interaction is weaker and has substantially larger degree of reversibility. In both solvents the polymer has a large available surface area, which is of great importance for the possibility of using the polymer-medetomidine complex in a paint formulation. When exposed to water the medetomidine in the surface layer dissociates from the Polystyrene-block-poly(ethylene-ran-butylene)-block-polystyrene and desorbs from the surface. A surface-active compound in antifouling paint is thus likely to have a greater impact on settlements of barnacle larvae than a compound leaking out of the paint into the water since surface activity will increase the concentration close to the surface.

This system is free of metal and metal oxides and decreases the damage to the marine ecosystem including animal species, plants and humans.

Polymer membranes containing sulfonic acid groups can generate ionic crosslinking with polymers containing heterocyclic rings such as imidazole, thus strong interactions.

For example, Medetomidine in one embodiment of the invention is comparatively harmless compared with the toxic substances presently used in ship hull paints. Indeed, Medetomidine is so harmless that it is approved in pharmaceutical preparations for internal use. Medetomidine is also biodegradable so it is less bio-accumulated and therefore ecologically safer than many existing antifouling compounds.

The invention herein can also be applied to polymers modified by other acids, such as acid sulphate ester, phosphonic acid, carboxylic acid or acid phosphate ester, to bind imidazole containing compounds,.

EXAMPLE 1

Binding and Release Studies

Preparation of Samples for Binding Studies

The binding studies of Medetomidine (Orion Pharma, Helsinki, Finland) and the sulfonated der-PS (sulfonated der-PS can be obtained from Sigma-Aldrich) were performed in o-xylene for different polymer: Medetomidine ratios (polymer:medetomidine, 0:1, 5:1, 10:1, 15:1, 30:1, 50:1, 100:1). The general procedure (the example shown is for the ratio 5:1) is as follows: 1 g o-xylene, 2.5 mg polymer (50 mg sol. from a 0.05 g/g sol.) and 0.5 mg Medetomidine in 1 ml o-xylene were mixed and placed on a shaker over night (for 0:1, 1 g o-xylene, 0.5 mg Medetomidine were dissolved in 1 ml o-xylene). The following day a 500 micro-liter sample was taken, the solvent was evaporated and another 500 micro-liter o-xylene was added. The sample was placed in an ultrasonic bath for 20 min and thereafter a 50 micro-liter sample was taken, the solvent was evaporated once again and 500 micro-liter MilliQ-water was added. The water sample was placed in an ultrasonic bath for another 20 min and then analysed with regards to its Medetomidine content using HPLC-UV system.

Binding Studies Analysis with HPLC

The UV-absorbance maximum of Medetomidine was, from the literature, found to be 220 nm. Prior to the HPLC analysis the UV-absorbance maximum was investigated in order to verify the value given from the literature using a UV-spectrometer (GBC 920 UV/visible spectrometer, Scientific Equipments Ltd., Victoria, Australia).

The samples were analysed on a HPLC-UV system consisting of a Merck-Hitachi L-6200 pump (Merck-Hitachi, Darmstadt, Germany), a Supelco Discovery® (Sigma-Aldrich Sweden AB, Stockholm, Sweden) C18 (25 cm×4.6 mm, 5 m) column fitted with a prefilter (0.5 μm) and a Spectra-Physics Spectra 100 UV (Spectra-Physics Inc, Irvine Calif., USA) operating at 220 nm. The mobile phase was MilliQ-water:Acetonitrile (0.1% TFA v/v (mobile phase A): 0.1% TFA v/v (mobile phase B)) run over a gradient (6% B for two min then a increase up to 60% B in 15 min, a further increase up to 100% B in 3 min and then isocratic for 3 min before returning to the starting values in 2 min) at a flow rate of 10 ml/min. The peak separation was monitored by UV (220 nm). Manual injections of 100 micro-liter were made and the data was collected and integrated using the Millenium software (version 3.20, 1999) (Waters Inc, Milford Mass., USA).

Preparation of Paint for Release Rate Studies

The SPC Lefant marine paint from Lotrec AB (Lindingo, Sweden) was used in the release rate studies. The paint was modified in two different ways: 1) addition of Medetomidine; or 2) addition of Medetomidine and the sulfonated der-PS. The non-modified paint served as control. The Medetomidine concentration in the paints was 0.1 wt % and the general procedure was as following: The polymer and Medetomidine were mixed and stirred for 5 minutes, thereafter the solvent was evaporated in order to achieve a saturated solution. The paint was then added, stirred for 5 min and placed on a shaker over night.

Painting the Panels

Before being painted, the test-panels were washed with cleaning powder (Deconnex®) (Borer Chemie, Zuchwil, CH) and the surface was coarsened by sandblasting. The painted area measured 11×7.5 cm (82.5 $cm^2$) and for each modification three panels were painted. The paint was applied using a 4-sided applicator (with gap sizes of 50, 100, 150 and 200 μm)

giving the possibility to control the paint film thickness. First a 50 μm primer film was applied and secondly a 200 μm paint film was applied. The panels were placed in 50 ml artificial seawater (pH 8) and on a shaker. Samples were taken each week during an eight week period.

Sampling for Release Rate Studies

After each week 0.1% TFA (500 micro-liter) was added to the artificial seawater. The water was then poured into falcon tubes (50 ml) and a 7 ml sample was taken up which was subsequently filtered through a syringe filter. The samples were placed in an ultrasonic bath for 20 min and analysed with HPLC.

Release Rate analysis with HPLC

The same system used in the binding studies above was also used for the Release rate studies but with a different gradient (from the starting values of A:B (94:6) an increase up to 60% B in 30 min was performed before a further increase up to 100% B in 5 min. These values were maintained for another 5 min. The % A was then increased in 5 min in order to generate the starting values, 94:6) at a flow rate of 1 ml/min. Manual injections of 1 ml were made and 2 ml samples spiked with Medetomidine (20 micro-liter from a 100 microM solution) were used to identify the correct peak.

Results

Figure 2:
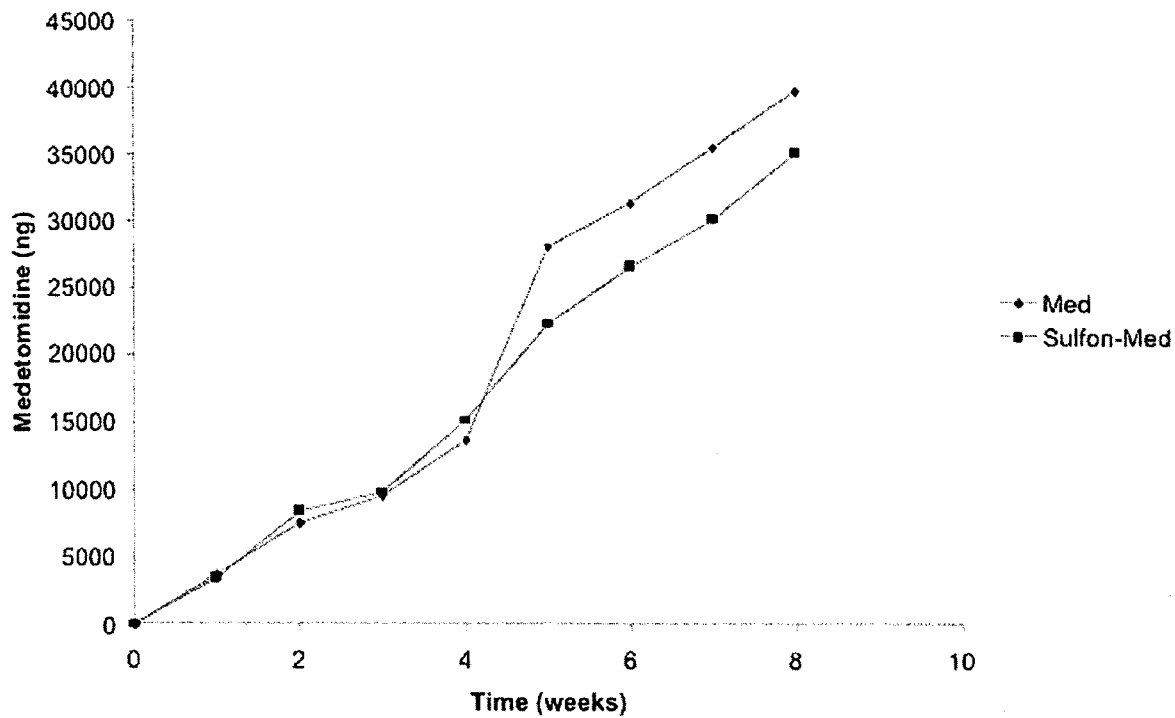
FIG. 2 shows a plot of the amount of released Medetomidine (ng) versus time (weeks) for Medetomidine-sulfonated der-PS and Medetomidine modified marine paints.

In FIG. 2 the amount Medetomidine released from the two SPC-paints is plotted against time (weeks). The Medetomidine-SPC-paint (type 1, as defined in "preparation of the paint for release rate studies" above in this example) and Medetomidine-sulfonated der-PS SPC paint (type 2, as per above) exhibit, after one week, similar amounts of released Medetomidine, $3.71 \times 10^3$ ng and $3.45 \times 10^3$ ng, respectively. During the remaining weeks of the first half of the investigation period, the two paints continued to exhibit comparable release rates, $3.39 \times 10^3$ ng week$^{-1}$ for the Medetomidine-SPC-paint and $3.55 \times 10^3$ ng week$^{-1}$ for the Medetomidine-sulfonated der-PS modified paint, and by the fourth week they reached a total amount of $1.37 \times 10^4$ and $1.51 \times 10^4$ ng, respectively. However after the fourth week an increase in amount Medetomidine released rate was seen for the Medetomidine-SPC-paint, from $1.37 \times 10^4$ to $2.81 \times 10^4$ ng. This can be compared to the Medetomidine-sulfonated der-PS modified paint, which only displayed a $0.71 \times 10^4$ ng increase corresponding to approximately half of the Medetomidine-SPC increase. This sudden increase in released amount for the Medetomidine-SPC-paint may be caused by the dissolution of an oxide or bacterial film covering the paint surface. After this increase the rates once again return to the same release rate, $3.39 \times 10^3$ ng weeks$^{-1}$ for the Medetomidine-SPC-paint and $3.55 \times 10^3$ ng weeks$^{-1}$ for the Medetomidine-sulfonated der-PS modified paint, which are equivalent to the rates displayed during the three initial weeks. Subsequently (after eight weeks) a total released amount of $3.97 \times 10^4$ ng for the Medetomidine modified SPC-paint and $3.51 \times 10^4$ ng for the Medetomidine-sulfonated der-PS modified SPC-paint was obtained, corresponding to a 12% difference.

What is claimed is:

1. A method of preventing marine biofouling of a substrate by a marine biofouling organism, comprising applying a protective coating to the substrate, said coating containing an imidazole-containing compound bound to a polymer backbone selected from the group consisting of polystyrene and acrylate polymers, said polymer backbone modified by being bound to a sulfonated substance.

2. The method of claim 1, wherein the sulfonated substance is a sulfonated acid.

3. The method of claim 1, wherein the sulfonated substance is selected from the group consisting of sulfonated acid sulphate ester, sulfonated phosphonic acid, sulfonated carboxylic acid and sulfonated acid phosphate ester.

4. The method of claim 1, wherein the polymer backbone is polystyrene.

5. The method of claim 1, wherein the imidazole-containing compound is Medetomidine.

6. The method of claim 1, wherein the protective coating further comprises a marine paint.

7. The method of claim 1, wherein the sulfonated substance is selected from the group consisting of sulfonated acid sulphate ester, phosphonic acid, carboxylic acid and acid phosphate ester, the polymer backbone is polystyrene, and the imidazole-containing compound is Medetomidine.

8. A product for preventing marine biofouling of a substrate by a marine biofouling organism, comprising a protective coating, said coating containing an imidazole-containing compound bound to a polymer backbone selected from the group consisting of polystyrene and acrylate polymers, said polymer backbone modified by being bound to a sulfonated substance.

9. The product of claim 8, wherein the sulfonated substance is a sulfonated acid.

10. The product of claim 8, wherein the sulfonated substance is selected from the group consisting of sulfonated acid sulphate ester, sulfonated phosphonic acid, sulfonated carboxylic acid and sulfonated acid phosphate ester.

11. The product of claim 8, wherein the polymer backbone is polystyrene.

12. The product of claim 8, wherein the imidazole-containing compound is Medetomidine.

13. The product of claim 8, wherein the protective coating further comprises a marine paint.

14. The product of claim 8, wherein the sulfonated substance is selected from the group consisting of sulfonated acid sulphate ester, phosphonic acid, carboxylic acid and acid phosphate ester, the polymer backbone is polystyrene, and the imidazole-containing compound is Medetomidine.

* * * * *